United States Patent [19]

Takuma et al.

[11] Patent Number: 5,182,409
[45] Date of Patent: Jan. 26, 1993

[54] PREPARATION PROCESS OF BIS(1,2-DIARYL-1,2-ETHYOLENEDITHIOLATO)NICKEL-BASED COMPLEX

[75] Inventors: Keisuke Takuma; Yoshihiro Irizato; Kimitoshi Katho, all of Ohmuta, Japan

[73] Assignee: Mitsui Toatsu Chemicals Inc., Tokyo, Japan

[21] Appl. No.: 613,554

[22] PCT Filed: Apr. 4, 1990

[86] PCT No.: PCT/JP90/00452
§ 371 Date: Nov. 15, 1990
§ 102(e) Date: Nov. 15, 1990

[87] PCT Pub. No.: WO90/12019
PCT Pub. Date: Oct. 18, 1990

[30] Foreign Application Priority Data

Apr. 5, 1989 [JP] Japan ................................ 1-84890
Dec. 27, 1989 [JP] Japan ................................ 1-336608

[51] Int. Cl.⁵ .............................................. C07F 17/02
[52] U.S. Cl. ........................................ 556/146; 556/138
[58] Field of Search .......................... 556/146, 138, 136

[56] References Cited

U.S. PATENT DOCUMENTS 4,806,664  2/1989  Schrott et al. ...................... 556/136

FOREIGN PATENT DOCUMENTS 61-225192  10/1986  Japan .
63-227597   9/1988  Japan .

OTHER PUBLICATIONS

Kijitani et al., "Effect of substituents in the aryl moiety of bis(1,2-diaryl-1,2-ethylenedithiolato)-nickel on the quenching of singlet oxygen and the reaction with singlet oxygen", Nippon Chemical Journal, vol. 1985, No. 3, pp. 433-437 (1985).
Chemical Abstracts, vol. 92, No. 16 (1980), Abstract No. 139914u.

Primary Examiner—Arthur C. Prescott
Attorney, Agent, or Firm—Millen, White & Zelano

[57] ABSTRACT

The present invention is a process for the preparation of bis(1,2-diaryl-1,2-ethylenedithiolato)-nickel-based complex which is characterized by reacting a benzil-based compound or a benzoin-based compound with phosphorus pentasulfide in 1,3-dimethyl-2-imidazolidinone and successively reacting with nickel chloride.

5 Claims, No Drawings

PREPARATION PROCESS OF BIS(1,2-DIARYL-1,2-ETHYOLENEDITHIOLATO)-NICKEL-BASED COMPLEX

1. TECHNICAL FIELD

The present invention relates to a process for the preparation of bis(1,2-diaryl-1,2-ethylenedithiolato)-nickel-based complex from benzil-based compounds or benzoin-based compounds.

2. BACKGROUND ART

Bis(1,2-diaryl-1,2-ethylenedithiolato)nickel-based complexes are compounds having characteristic absorption in the near-infrared region. These are a group of compounds used for light compensation filters for near-infrared radiation and optical recording discs. These complexes also have a property for deactivating a singlet oxygen and are employed for singlet oxygen quenchers such as light stabilizers or antioxidants of polyolefins and photodeterioration inhibitors of organic dyestuffs.

The common preparation process of these complexes is described, for example, in G. N. Schrauzer et al, J. Am. Chem. Soc., 87, 1483 (1965) and can be prepared by the following reaction process.

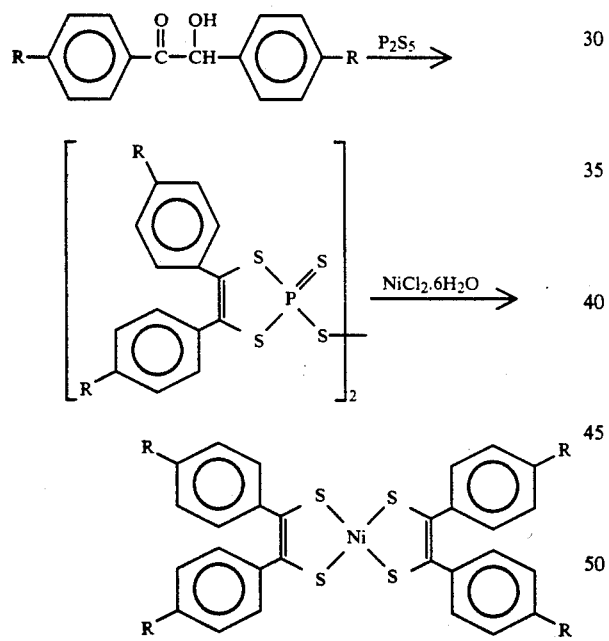

That is, a benzoin compound represented by the formula (III):

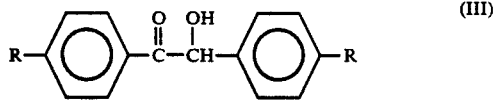

wherein R is a hydrogen atom, methyl, methoxy or a chlorine atom, and is reacted with phosphorus pentasulfide by heating in dioxane. An intermediate phosphorus compound thus formed is cooled to the room temperature. After filtering off insoluble by-products, an aqueous solution of nickel chloride (II) is added and reacted by heating to obtain a nickel-based complex represented by the formula (IV):

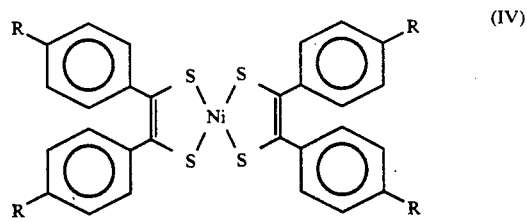

wherein R is the same as in the formula (III).

However, the process which uses dioxane as a solvent causes various side reactions and the desired product can be obtained in a low yield of about 35% at the most. Consequently, enhancement of the yield has been desired.

3. DISCLOSURE OF INVENTION

The object of the invention is to provide a preparation process for obtaining a bis(1,2-diaryl-1,2-ethylenedithiolato)nickel-based complex in a high yield by using a benzil-based compound or a benzoin-based compound as a raw material.

As a result of extensive investigation, it has been found that the object can be achieved by carrying out the reaction in a specific solvent. That is, the aspect of the invention is a process for the preparation of a bis(1,2-diaryl-1,2-ethylenedithiolato)nickel-based complex by reacting the above raw material with phosphorus pentasulfide in 1,3-dimethyl-2-imidazolidinone and successively reacting the resultant intermediate with nickel chloride.

4. BEST MODE FOR CARRYING OUT THE INVENTION

The bis(1,2-diaryl-1,2-ethylenedithiolato)nickel-based complex which is the object of the present invention is represented by the formula (I):

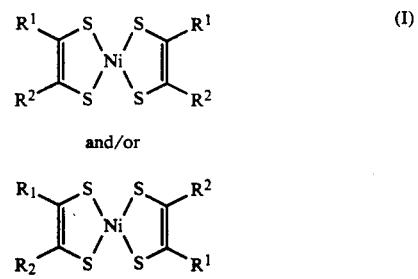

where $R^1$ and $R^2$ are individually phenyl or naphthyl and may also have from one to three substituents individually selected from alkyl, cycloalkyl, aryl, alkoxy, phenoxy, hydroxy, alkylamino, arylamino, trifluoromethyl, alkylthio, arylthio, nitro, cyano, heterocycle or halogen atoms, and these substituents may connect with each other to form a ring.

The benzil- or benzoin-based compound used as a starting material is a compound having $R^1$ and $R^2$ which corresponds to the above formula (I) and is represented by the formula (II):

wherein X is C=O in the case of the benzil-based compound or CHOH in the case of the benzoin-based compound.

Representative examples of the group, heterocycle and atoms which can be used as the substituents in the above $R^1$ and $R^2$ include alkyl group such as methyl, ethyl, butyl, pentyl and hexyl; cycloalkyl groups such as cyclopentyl and cyclohexyl; non-substituted or substituted aryl groups such as phenyl and p-nitrophenyl; alkoxy groups such as methoxy, ethoxy and butoxy; phenoxy; hydroxy; alkylamino groups such as dimethylamino, diethylamino and dibutylamino; arylamino groups such as diphenylamino and ditolylamino; trifluoromethyl; alkylthio groups such as methylthio, ethylthio and butylthio; arylthio groups such as phenylthio and tolylthio; nitro; cyano; heterocycles such as

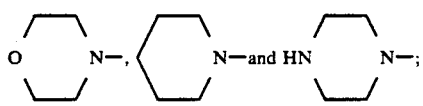

and halogen atoms such as fluorine, chlorine, bromine and iodine. Representative examples of the ring which is formed by connecting include alkylene and alkylenedioxy.

The compound of the above formula (I) is prepared by the following process: One mole of the benzyl- or benzoin-based compound having $R^1$ and $R^2$ corresponding to those of the formula (I) and represented by the formula (II) (hereinafter referred to as the raw material compound), and from 1 to 5 moles, preferably from 1.2 to 2 moles of phosphorus pentasulfide are dissolved or suspended in 1,3-dimethyl-2-imidazolidinone (hereinfter abbreviated as DMI). DMI is used in an amount of 1 to 100 parts by weight, preferably 4 to 20 parts by weight per part by weight of the raw material compound. The mixture obtained is heated to 50° to 160° C., preferably 70° to 120° C., to form the intermediate phosphorus compound.

The reaction mixture is then cooled to 70° C. to room temperature. An aqueous solution containing 0.4 to 2 moles, preferably 0.4 to 0.6 mole of nickel chloride (II) hexahydrate per mole of the raw material compound is added to the reaction mixture thus obtained and reacted at a temperature of 10° to 160° C., preferably 40° to 120° C. The resulting reaction mixture is then poured into water, alcohol or acetone, filtered, washed with alcohol, washed with water, and dried. Alternatively, the reaction mixture is further concentrated and separated, the precipitate is filtered, washed with alcohol, washed with water, and dried. Thus, a mixture of the two isomers represented by the formula (I) can be obtained in high yield.

The benzil-based compound, one of the starting materials, can readily give compounds which are substituted with a long chain alkyl, long chain alkoxy or secondary amino group by using the Friedel Crafts reaction. These compounds are difficult to obtain by benzoin condensation.

DMI used in the present invention has low toxicity, is thermally and chemically stable, has a high boiling point of 225° C., a high flash point of 107° C., a low solidifying point of 82° C. and can be handled with ease. Further, DMI has strong dissolving power for inorganic and organic compounds and is capable of converting the reactants to a readily reactable form due to its high dielectric constant and solvation effect. Hence, DMI is deemed to be effective for ionic reactions such as the synthesis of the nickel complex of the present invention.

In the above DMI solvent method, the intermediate phosphorus compound is obtained without formation of insoluble by-products, and the next reaction can be successively carried out without filtration. Consequently, the process of the present invention is very advantageous in industry.

EXAMPLE

The present invention will hereinafter be illustrated by way of examples. Parts and % in the examples are parts by weight and % by weight, respectively. The purity of the desired product was measured by using toluene eluate (Trade Mark; Iatroscan TH-10, a product of Iatron Co., Ltd.).

EXAMPLE 1

A mixture of 5 parts of benzil, 7.5 parts of phosphorus pentasulfide and 35 parts of DMI were reacted at 100° to 105° C. for 2 hours. The reaction mixture was cooled to 60° C. The solution obtained by dissolving 2.8 parts of nickel chloride (II) hexahydrate in 10 parts of water was added to the reaction mixture and reacted at 90° C. for 2 hours. The resulting reaction mixture was cooled to room temperature and poured into 150 parts of ethanol. The precipitate was filtered, washed with ethanol, washed with warm water and dried to obtain 4.6 parts of the compound having the following formula:

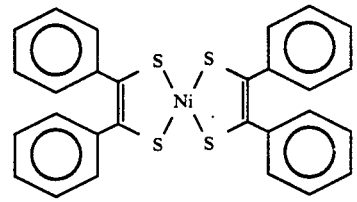

The yield was 72% and purity was 99.7%.
Appearance: Greenish black cyrstalline powder
Maximum absorption wave length λmax=855 nm (chloroform)
Melting point=292°-293° C. (Bibliographic data 292° C.)

EXAMPLE 2

The same procedures as conducted in Example 1 were carried out by using 6.4 parts of anisil in place of benzil to obtain 5.8 parts of the compound having the following formula:

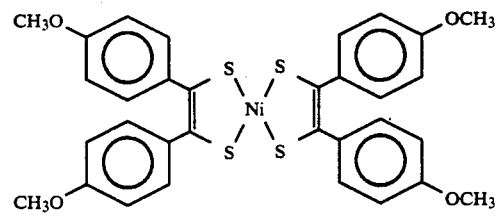

The yield was 70% and the purity was 99.6%.

Appearance: Greenish black crystalline powder
Maximum absorption wave length λmax=920 nm (chloroform)
Melting point=328°-329° C. (decomposition) (Bibliographic data 329° C.)

EXAMPLES 3-34

The same procedures as conducted in Example 1 were carried out except that benzil was replaced by various benzil-based compounds having the formula (II) wherein X is C=O, and $R^1$ and $R^2$ were as illustrated in Table 1.

Various compounds of the invention represented by formula (I) wherein $R^1$ and $R^2$ were as illustrated in Table 1 were obtained in high yield.

TABLE 1

| Example | $R^1$ and $R^2$ | Yield (%) |
|---|---|---|
| 3 | CH₃—⌬— | 76 |
| 4 | C₂H₅—⌬— | 76 |
| 5 | n-C₄H₉—⌬— | 75 |
| 6 | C₁₂H₂₅—⌬— | 72 |
| 7 | (CH₃)₃C—⌬— | 72 |
| 8 | 2,3-(CH₃)₂—⌬— | 73 |
| 9 | (H₃C)₃C—⌬—CH₃ | 64 |
| 10 | C₂H₅O—⌬— | 71 |
| 11 | C₄H₉O—⌬— | 74 |
| 12 | cyclohexyl—⌬— | 74 |
| 13 | cyclohexyl—⌬— (H substituent) | 74 |
| 14 | biphenyl— | 72 |
| 15 | ⌬—O—⌬— | 72 |
| 16 | naphthyl— | 65 |
| 17 | methylnaphthyl— | 63 |
| 18 | H₃CO—naphthyl— | 62 |
| 19 | CF₃—⌬— | 62 |
| 20 | CH₃S—⌬— | 68 |
| 21 | ⌬—S—⌬— | 72 |
| 22 | O₂N, H₃CO substituted phenyl— | 65 |

TABLE 1-continued

| Example | R¹ and R² | Yield (%) |
|---|---|---|
| 23 | (H₃C)₂N-C₆H₄- | 58 |
| 24 | morpholino-C₆H₄- | 56 |
| 25 | (C₆H₅)₂N-C₆H₄- | 66 |
| 26 | 3-F, 4-Cl-C₆H₃- | 72 |
| 27 | 3-H₃CO, 4-Cl-C₆H₃- | 72 |
| 28 | 3-H₃CO, 4-NC-C₆H₃- | 70 |
| 29 | 4-HO-C₆H₄- | 70 |
| 30 | 2-Cl, 4-H₃CO-C₆H₃- | 68 |
| 31 | 2-Br, 4-H₅C₂-C₆H₃- | 68 |
| 32 | 3-CH₃O, 4-Cl-C₆H₃- | 74 |
| 33 | 3,4-(CH₃O)₂-C₆H₃- | 74 |
| 34 | 3,4-(-O-CH₂-CH₂-O-)-C₆H₃- | 72 |

EXAMPLE 35

A mixture of 5 parts of benzoin, 7.5 parts of phosphorus pentasulfide and 3.5 parts of DMI were reacted at 100° to 105° C. for 2 hours. The reaction mixture was cooled to room temperature. A solution obtained by dissolving 2.8 parts of nickel chloride (II) hexahydrate in 10 parts of water was added to the reaction mixture and reacted at 90° C. for 2 hours. The resulting reaction mixture was cooled to room temperature and poured into 150 parts of ethanol. The precipitate was filtered, washed with ethanol, washed with warm water and dried to obtain 5.0 parts of a compound having the following formula:

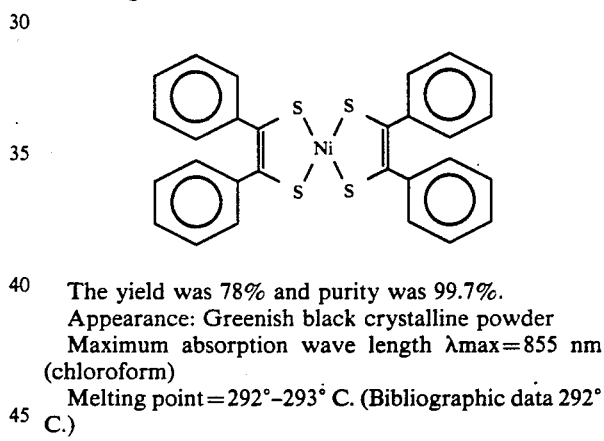

The yield was 78% and purity was 99.7%.
Appearance: Greenish black crystalline powder
Maximum absorption wave length λmax=855 nm (chloroform)
Melting point=292°-293° C. (Bibliographic data 292° C.)

EXAMPLE 36

The same procedures as conducted in Example 35 were carried out except that 6.4 parts of anisoin was used in place of benzoin and was reacted at 50° C. for an hour after the addition of nickel chloride. The reaction mixture was further reacted at 90°±5° C. for 2 hours to obtain 5.8 parts of a compound having the following formula:

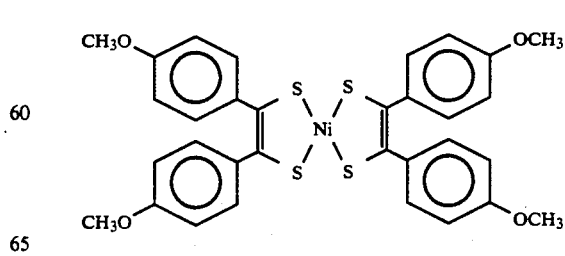

The yield was 74% and purity was 99.4%.
Appearance: Greenish black crystalline powder Maximum absorption wave length λmax=920 nm (chloroform) Melting point=328°-329° C. (decomposition) (Bibliographic data 329° C.)

EXAMPLE 37-75

The same procedures as conducted in Example 35 were carried out except that benzoin was replaced by various benzoin-based compounds having the formula (II) wherein X is CHOH, and $R^1$ and $R^2$ were as illustrated in Table 2.

Various compounds of the invention represented by the formula (I) wherein $R^1$ and $R^2$ were as illustrated in Table 2 were obtained in high yield.

TABLE 2

| Example | $R^1$ | $R^2$ | Yield (%) |
|---|---|---|---|
| 37 | CH₃—⌬— | *1) | 76 |
| 38 | CH₃—⌬— | —⌬ | 77 |
| 39 | C₂H₅—⌬— | * | 77 |
| 40 | n-C₄H₉—⌬— | * | 74 |
| 41 | (CH₃)₃C—⌬— | * | 75 |
| 42 | 2,4,6-(CH₃)₃-C₆H₂— | * | 72 |
| 43 | CH₃O—⌬— | —⌬ | 75 |
| 44 | C₂H₅O—⌬— | * | 71 |
| 45 | C₄H₉O—⌬— | * | 71 |
| 46 | H-cyclohexyl—⌬— | * | 76 |
| 47 | biphenyl— | * | 77 |
| 48 | O₂N—⌬—⌬— | * | 70 |
| 49 | ⌬—O—⌬— | * | 72 |
| 50 | naphthyl— | * | 69 |
| 51 | methylnaphthyl— | * | 70 |
| 52 | CF₃—⌬— | * | 71 |
| 53 | CH₃S—⌬— | * | 71 |
| 54 | ⌬—S—⌬— | * | 70 |
| 55 | O₂N—⌬— | * | 70 |
| 56 | (H₃C)₂N—⌬— | * | 69 |
| 57 | (H₃C)₂N—⌬— | —⌬ | 68 |

TABLE 2-continued

| Example | R¹ | R² | Yield (%) |
|---|---|---|---|
| 58 | 4-(diphenylamino)phenyl | * | 66 |
| 59 | 4-F-C₆H₄- | * | 75 |
| 60 | 4-F-C₆H₄- | C₆H₅- | 76 |
| 61 | 4-Br-C₆H₄- | * | 70 |
| 62 | 4-Br-C₆H₄- | C₆H₅- | 71 |
| 63 | 4-I-C₆H₄- | C₆H₅- | 68 |
| 64 | 4-Cl-C₆H₄- | * | 74 |
| 65 | 4-Cl-C₆H₄- | C₆H₅- | 75 |
| 66 | 4-NC-C₆H₄- | * | 74 |
| 67 | 4-HO-C₆H₄- | C₆H₅- | 69 |
| 68 | 3,4-di-Cl-C₆H₃- | * | 72 |
| 69 | 2-Cl-C₆H₄- | * | 68 |
| 70 | 2-Br-C₆H₄- | * | 73 |
| 71 | 3-Cl-4-CH₃O-C₆H₃- | * | 74 |
| 72 | 3,4-di-Cl-C₆H₃- | * | 74 |
| 73 | 3,4,5-tri-CH₃O-C₆H₂- | * | 72 |
| 74 | 3,4-di-CH₃O-C₆H₃- | 2-Cl-C₆H₄- | 74 |
| 75 | 3,4-methylenedioxyphenyl | * | 76 |

Note ¹⁾* indicates that R² is the same as R¹.

COMPARATIVE EXAMPLE 1

The same procedures as conducted in Example 35 were carried out except that dioxane was used in place of DMI and the insoluble matter was removed by filtration after reacting for 2 hours (before the addition of nickel chloride).

The yield of the greenish black crystalline powder thus obtained was only 35%.

COMPARATIVE EXAMPLE 2

The procedures of Example 35 were repeated by using N,N-dimethylformamide in place of DMI. However, the desired product could not be obtained.

COMPARATIVE EXAMPLE 3

The procedures of Example 35 were repeated by using dimethylsulfoxide in place of DMI. However, the desired product could not be obtained at all.

INDUSTRIAL APPLICABILITY

According to the process of the present invention, the near-infrared absorbable bis(1,2-diaryl-1,2-ethylenedithiolato)nickel-based complex can be obtained in high yield. The complex is useful for near-infrared filters of electronic equipment and photography, safety goggles, sunglasses, goggles, heat insulation films, agricultural films, photo discs, optical character readers, solar heat storage, and photosensitive materials. Therefore, the process of the invention has extremely high potential for industrial applications.

We claim:

1. A preparation process of bis(1,2-diaryl-1,2-ethylenedithiolato)nickel-based complex represented by the formula (I):

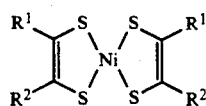

and/or

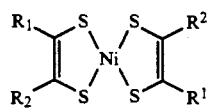

wherein $R^1$ and $R^2$ are individually phenyl or naphthyl and may also have from one to three substituents individually selected from alkyl, cycloalkyl, aryl, alkoxy, phenoxy, hydroxy, alkylamino, arylamino, trifluoromethyl, alkylthio, arylthio, nitro, cyano, heterocycle or halogen atoms and these substituents may connect with each other to form a ring, which is characterized by reacting the compound represented by the formula (II):

wherein $R^1$ and $R^2$ are the same as in the formula (I) and X is C=O or CHOH, with phosphorus pentasulfide in 1,3-dimethyl-2-imidazolidinone and successively reacting with nickel chloride.

2. The preparation process of claim 1 wherein X in the formula (II) is C=O.

3. The preparation process of claim 1 wherein X in the formula (II) is CHOH.

4. A process according to claim 1 wherein at least one of $R^1$ and $R^2$ is individually phenyl and independently substituted by 1 to 3 hydroxy, phenoxy, alkylthio, arylthio, nitro, cyano, a heterocycle, alkylamino, arylamino or trifluormethyl, or said substituents connected with each other to form a ring.

5. A process according to claim 1 wherein $R^1$ and $R^2$ are individually naphthyl and may also have one to three substituent individually selected from the group consisting of alkyl, cycloalkyl, aryl, alkoxy, phenoxy, hydroxy, alkylamino, arylamino, trifluoromethyl, alkylthio, arylthio, nitro, cyano, a heterocycle, halogen and these substituents connected with each other to form a ring.

* * * * *